United States Patent
Foussat

(10) Patent No.: US 9,517,253 B2
(45) Date of Patent: *Dec. 13, 2016

(54) COMPOSITIONS FOR TREATING MULTIPLE SCLEROSIS

(75) Inventor: Arnaud Foussat, Biot (FR)

(73) Assignee: TXCELL, Valbonne (FR)

( * ) Notice: Subject to any disclaimer, the term of this patent is extended or adjusted under 35 U.S.C. 154(b) by 852 days.

This patent is subject to a terminal disclaimer.

(21) Appl. No.: 12/738,706

(22) PCT Filed: Oct. 17, 2008

(86) PCT No.: PCT/EP2008/064066
§ 371 (c)(1),
(2), (4) Date: Apr. 19, 2010

(87) PCT Pub. No.: WO2009/050283
PCT Pub. Date: Apr. 23, 2009

(65) Prior Publication Data
US 2010/0221219 A1 Sep. 2, 2010

(30) Foreign Application Priority Data
Oct. 17, 2007 (EP) .................................. 07301475

(51) Int. Cl.
| | | |
|---|---|---|
| A61K 35/26 | (2015.01) | |
| A61K 38/21 | (2006.01) | |
| A61K 35/17 | (2015.01) | |
| A61K 31/00 | (2006.01) | |
| A61K 39/00 | (2006.01) | |
| C12N 5/0783 | (2010.01) | |

(52) U.S. Cl.
CPC ............ *A61K 38/212* (2013.01); *A61K 31/00* (2013.01); *A61K 35/17* (2013.01); *A61K 39/0008* (2013.01); *C12N 5/0637* (2013.01); *A61K 2039/5158* (2013.01)

(58) Field of Classification Search
CPC  A61K 35/17; A61K 35/26; A61K 2039/5158; C12N 5/0637
See application file for complete search history.

(56) References Cited

U.S. PATENT DOCUMENTS

| | | |
|---|---|---|
| 6,746,670 B2 | 6/2004 | Levings |
| 2002/0090357 A1 | 7/2002 | Barrat |
| 2004/0087018 A1 | 5/2004 | Barrat et al. |
| 2004/0191235 A1 | 9/2004 | Groux |
| 2006/0057110 A1 | 3/2006 | Eisenbach-Schwartz et al. |

FOREIGN PATENT DOCUMENTS

| | | |
|---|---|---|
| EP | 0 587 735 | 1/2000 |
| EP | 1 739 166 | 1/2007 |
| WO | 96/27387 | 9/1996 |
| WO | 02/077025 | 10/2002 |
| WO | 02092793 | 11/2002 |
| WO | 2005/000344 | 1/2005 |
| WO | 2006050138 | 5/2006 |
| WO | 2006/108882 | 10/2006 |

OTHER PUBLICATIONS

Geysen et al., J. Molecular Recognition 1 (1): 32-41 (1988).*
International Search Report dated Mar. 10, 2009, from corresponding PCT application.
Barrat et al., "In Vitro Generation of Interleukin 10-producing Regulatory CD4+ T Cells Is Induced by Immunosuppressive Drugs and Inhibited by T Helper Type 1 (Th1)- and Th2-inducing Cytokines", J. Exp. Med., The Rockefeller University Press, Mar. 4, 2002, vol. 195, No. 5, pp. 603-616.
Rizvi et al., "Glatiramer in the treatment of multiple sclerosis", International Journal of Nanomedicine. 2006;1(3), pp. 283-289.
Manganas et al., "Stem Cell Therapy for Central Nervous System Demyelinating Disease", Curr Neurol Neurosci Rep. May 2005;5(3):225-31.
Groux et al., "Regulatory T cells and inflammatory bowel disease", Immunology today. Oct. 1999, vol. 20 No. 10, pp. 442-445.
Chaudhuri et al., "Treatment of multiple sclerosis: beyond the NICE guidelines", QJM. May 2005;98(5), pp. 373-378.
Virley, "Developing Therapeutics for the Treatment of Multiple Sclerosis", NeuroRx. Oct. 2005; vol. 2, pp. 638-649.
Kort et al., "Efficient presentation of myelin oligodendrocyte glycoprotein peptides but not protein by astrocytes from HLA-DR2 and HLA-DR4 transgenic mice", Journal of Neuroimmunology, 2006, 173(1):23-24.
Bielekova et al., "Encephalitogenic potential of the myelin basic protein peptide (amino acids 83-99) in multiple sclerosis: Results of a phase II clinical trial with an altered peptide ligand", Nature Med. Oct. 2000, vol. 6 No. 10, pp. 1167-1175.
Zajicek et al., "Diagnosis and disease modifying treatments in multiple sclerosis", Postgrad Med J., Sep. 2005;81(959):556-561.
Majewska et al., "Epicutaneous immunization with myelin basic protein protects from the experimental autoimmune encephalomyelitis", Pharmacological Reports, Jan.-Feb. 2007;59(1):74-79.
Wildbaum et al., "Tr1 cell-dependent active tolerance blunts the pathogenic effects of determinant spreading", The Journal of Clinical Investigation, Sep. 2002, vol. 110 No. 5; pp. 701-710.
Polman et al., "A randomized, placebo-controlled trial of natalizumab for relapsing multiple sclerosis", The New England Journal of Medicine, Mar. 2, 2006; 354(9): pp. 899-910.
Adelmann et al., "The N-terminal domain of the myelin oligodendrocyte glycoprotein (MOG) induces acute demyelinating experimental autoimmune encephalomyelitis in the Lewis rat", Journal of Neuroimmunology, 1995, 63(1):17-27.
Glass-Marmor et al., "Chronotherapy using corticosteroids for multiple sclerosis relapses", J Neurol Neurosurg Psychiatry. Aug. 2007;78(8):886-888.

(Continued)

Primary Examiner — Robert C Hayes
(74) Attorney, Agent, or Firm — Young & Thompson

(57) ABSTRACT

Compositions comprising Tr1 cells directed to a multiple sclerosis associated antigen and methods for treating multiple sclerosis.

9 Claims, 2 Drawing Sheets

(56) References Cited

OTHER PUBLICATIONS

Hutchinson, "Natalizumab: A new treatment for relapsing remitting multiple sclerosis", Therapeutics Clinical Risk Management Jun. 2007;3(2):259-268.

Wakkach et al., "Differentiation of Regulatory T cells 1 is induced by CD2 Costimulation", The Journal Immunology 2001, 167(6):3107-3113.

Wingerchuk et al., "A pilot study of oral calcitriol (1,25-dihydroxyvitamin D3) for relapsing-remitting multiple sclerosis", J Neurol Neurosurg Psychiatry., Sep. 2005;76(9):1294-1296.

Ding et al., "B7H1-lg fusion protein activates the CD4+ IFN-gamma receptor + Type 1 T regulatory subset through IFN-gamma-secreting Th1 cells", The Journal of Immunology, 2006, 177:3606-3614.

Martin, "Is haematopoietic stem cell transplantation a treatment option for severe MS or not?", Brain. May 2007;130(Pt 5)1181-1182.

Cua et al., "Transgenic Interleukin 10 Prevents Induction of Experimental Autoimmune Encephalomyelitis", J. Exp. Med., Mar. 15, 1999, vol. 189 No. 6:1005-1010.

Kobayashi et al., "Antigen-specific suppression of experimental autoimmune encephalomyelitis by a novel bifunctional peptide inhibitor", The Journal Pharmacology and Experimental Therapeutics, Aug. 2007; vol. 322 No. 2: pp. 879-886.

Horwitz et al., "Regulatory T cells generated ex vivo as an approach for the therapy of autoimmune disease", Seminars in Immunology, 2004, 16(2):135-143.

Cross et al., "Rituximab reduces B cells and T cells in cerebrospinal fluid of multiple sclerosis patients", J. Neuroimmunol. Nov. 2006;180(1-2):63-70.

Roncarolo et al., "Interleukin-10 secreting type I regulatory T cells in rodents and humans", Immunological review, 2006, 212, p. 28-50.

Foussat et al., "A comparative study between T regulatory type 1 and CD4+CD25+ T cells in the control of inflammation", The Journal of Immunology, 2003, 171(10):5018-5026.

Mathey et al., "Neurofascin as a novel target for autoantibody-mediated axonal injury", The Journal of Experimental Medicine, Oct. 1, 2007; vol. 204 No. 10 : pp. 2363-2372.

Frenkel et al., "Nasal Vaccination with Myelin Oligodendrocyte Glycoprotein Reduces Stroke Size by Inducing IL-10-Producing CD4+ T Cells", The Journal of Immunology, 2003, 171:6549-6555.

Rudick et al., "Natalizumab plus interferon beta-1a for relapsing multiple sclerosis", The New England Journal Medicine, Mar. 2, 2006; 354(9):911-923.

Groux et al., "A CD4+ T-cell subset inhibits antigen-specific T-cell responses and prevents colitis" Nature. 1997, 389(6652):737-742.

Bertolotto et al., "Biological activity of interferon betas in patients with multiple sclerosis is affected by treatment regimen and neutralising antibodies", J Neurol Neurosurg Psychiatry. Sep. 2004;75(9):1294-1299.

Tenser, "Natalizumab for relapsing multiple sclerosis", The New England Journal of Medicine, Jun. 1, 2006;354(22):2387-9; author reply 2387-9.

Kappos et al., "Induction of a non-encephalitogenic type 2 T helper-cell autoimmune response in multiple sclerosis after administration of an altered peptide ligand in a placebo-controlled, randomized phase II trial", Nature Medicine 2000, vol. 6, No. 10:1176-1182.

Morales et al., "Treatment with an estrogen receptor alpha ligand is neuroprotective in experimental autoimmune encephalomyelitis", The Journal of Neuroscience, Jun. 21, 2006;26(25):6823-6833.

Yin et al., Chinese Journal of Immunology, 2002, 3:184-186 and 190.

Ichikawa et al., "Analysis of the fine B cell specificity during the chronic/relapsing course of a multiple sclerosis-like disease in Lewis rats injected with the encephalitogenic myelin oligodendrocyte glycoprotein peptide 35-55", J. Immunol. 1996, 157(2):919-926.

Klehmet et al., "T cell epitope spreading to myelin oligodendrocyte glycoprotein in HLA-DR4 transgenic mice during experimental autoimmune encephalomyelitis", Clinical immunology, 2004, 111(1):53-60.

Uyttenhove et al., "Development of an anti-IL-17A auto-vaccine that prevents experimental auto-immune encephalomyelitis", Eur. J. Immunol. Nov. 2006;36(11):2868-2874.

Astier et al., "Alterations in CD46-mediated Tr1 regulatory T cells in patients with multiple sclerosis", The Journal Clinical Investigation, Dec. 2006, vol. 116 No. 12: 3252-3257.

Kleinewietfeld et al., "Regulatory T cells in autoimmune neuroinflammation", Immunological Reviews, 2014, vol. 259: 231-244.

Stuve et al., "Immunomodulatory synergy by combination of atorvastatin and glatiramer acetate in treatment of CNS autoimmunity," The Journal of Clinical Investigation, Apr. 2006; vol. 116, No. 4:1037-1044.

Wakkach et al., "Characterization of dendritic cells that induce tolerance and T regulatory 1 cell differentiation in vivo", Immunity. May 2003, vol. 18(5):605-617.

Ephrem et al., "Expansion of CD4+CD25+ regulatory T cells by intravenous immunoglobulin: a critical factor in controlling experimental autoimmune encephalomyelitis", Blood. Jan. 15, 2008; vol. 111 No. 2:715-722. Originally published online Oct. 11, 2007.

Bettelli et al., "Myelin oligodendrocytes glycoprotein-specific T cell receptor transgenic mice develop spontaneous autoimmune optic neuritis", J. Exp. Med., May 5, 2003, 197(9), p. 1073-1081.

* cited by examiner

COMPOSITIONS FOR TREATING MULTIPLE SCLEROSIS

FIELD OF THE INVENTION

The present invention relates to the field of treatment of autoimmune disease, such as multiple sclerosis. More particularly, it concerns a medicament comprising Tr1 cells directed against multiple sclerosis-associated antigen.

BACKGROUND

Multiple sclerosis is a demyelinating and chronic inflammatory disease of the central nervous system. The histopathologic hallmarks of the disease include focal infiltration of both CD4+ and CD8+ T cells together with other inflammatory cells in the white matter and demyelination with evidence of some axonal damage. The myelin proteins thought to be the target of an immune response in multiple sclerosis include myelin basic protein (MBP), proteolipid protein (PLP), myelin associated glycoprotein (MAG) and myelin oligodendrocyte glycoprotein (MOG).

A variety of therapeutic approaches are now available in humans to treat multiple sclerosis. However, no curative treatments exist for multiple sclerosis. While a number of compounds, including corticosterioids and modified beta interferon, can reduce some symptoms of multiple sclerosis, they have proven to have serious side effects or otherwise been shown to be less than desirable for long term use.

One promising treatment for multiple sclerosis is described in WO 02/077025 which discloses the use of peptide analogs of myelin basic protein (MBP). Compositions comprising these analogs are reportedly able to ameliorate symptoms of MS without excessive side effects. Moreover, use of peptide analogs to myelin constitutive proteins were also shown to be effective in treating the symptoms of experimental allergic encephalomyelitis (EAE), an organ specific immune disorder often used in mice as a model for MS. However, several phase II clinical trials had to be halted due to the poor tolerance of the altered MBP peptide at the dose tested (Bielekova et al., nature medicine, 2000, (6) 10: 1167 et Kappos et al., nature medicine, 2000, (6) 10: 1176).

Another promising treatment for multiple sclerosis is also described in EP0587735. Said treatment is based on the rational that immunologic exposure to a peptide closely resembling an autoreactive TCR fragment should enhance Th2 cells priming/recognition, and thus help to maintain cytokine regulatory control over Th1-mediated inflammation. Clinical trials have demonstrated acceptable safety and tolerability of this treatment by the patients; however, this treatment is only effective on 50% of the immunized patients. US2004/0087018 describes a method for treating multiple sclerosis in a patient in need thereof, comprising administering antigen-specific IL-10 producing cells to said patient together with the soluble antigen, preferably simultaneously.

The inventors surprisingly found that the administration of Tr1 cells directed against a multiple sclerosis-associated antigen, without co-administration of the soluble antigen, dramatically inhibits the development of EAE in immunized mice.

Therefore, the Applicant aim to provide another type of treatment for multiple sclerosis based on the use of Tr1 cells.

SUMMARY OF THE INVENTION

The present invention is directed to a composition comprising at least one Tr1 cell population directed against a multiple sclerosis-associated antigen. Said multiple sclerosis-associated antigen is preferably selected from the group comprising myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins NOGO A, glycoprotein Po, peripheral myelin protein 22, 2'3'-cyclic nucleotide 3'-phosphodiesterase.

Another object of the present invention is to provide a medicament or a pharmaceutical composition comprising the composition of the invention.

The present invention relates also to a method for treating multiple sclerosis in a subject in need thereof, comprising administering to said subject an effective amount of the medicament or the pharmaceutical composition of the invention. In a preferred embodiment, the medicament or the pharmaceutical composition to be administered to a subject in need thereof comprises Tr1 cells autologous to the cells of said subject.

In another embodiment of the present invention, the method for treating multiple sclerosis in a subject in need thereof comprises the administration to said subject of an effective amount of the medicament or the pharmaceutical composition of the invention in combination with another therapeutic agent used for treating multiple sclerosis.

DETAILED DESCRIPTION OF THE INVENTION

Definition

Figure 1:
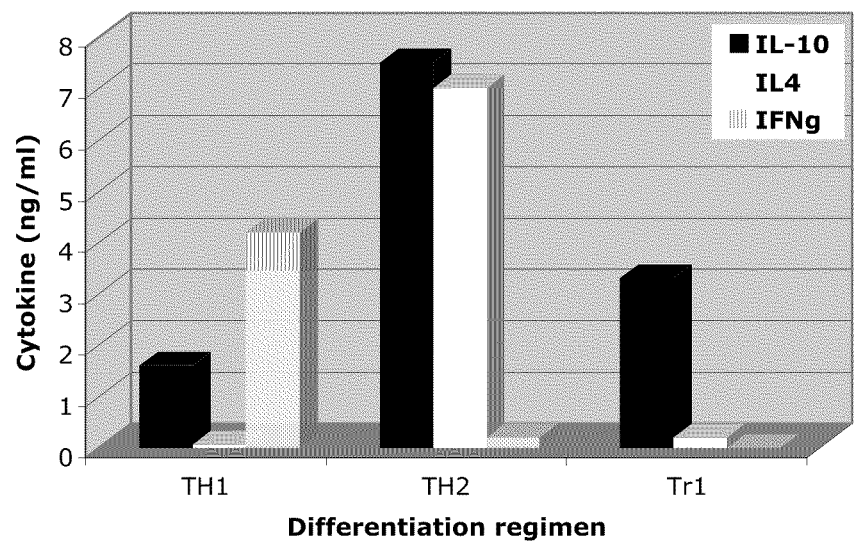
FIG. 1: Cytokine secretion profile of differentiated cells. Naïve CD4+ cells submitted to differentiation regimens were activated with anti-CD3+ anti-CD28 monoclonal antibodies during 48 hours. Culture supernatants were then tested by ELISA for the presence of IL-4, IL-10 and IFN-gamma.

The term "Tr1 cells" as used herein refers to cells having the following phenotype at rest CD4+CD25-FoxP3- and capable of secreting high levels of IL-10 and low to moderate levels of TGF-β upon, activation. Tr1 cells are characterized, in part, by their unique cytokine profile: they produce high levels of IL-10, significant levels of TGF-β and intermediate levels of IFN-γ, but little or no IL-4 or IL-2. The cytokine production is typically evaluated in cultures of cells after activation with polyclonal activators of T lymphocytes such as anti-CD3+ anti-CD28 antibodies or Interleukin-2, PMA+ ionomycin, Alternatively, the cytokine production is evaluated in cultures of cells after activation with the specific T-cell antigen presented by antigen presenting cells. High levels of IL-10 correspond to at least about 500 pg/ml, typically greater than about 1, 2, 4, 6, 8, 10, 12, 14, 16, 18, or 20 thousand pg/ml or more. Significant levels of TGF-β correspond to at least about 100 pg/ml, typically greater than about 200, 300, 400, 600, 800, or 1000 pg/ml or more. Intermediate levels of IFN-γ correspond to concentrations comprised between 0 pg/ml and at least 400 pg/ml, typically greater than about 600, 800, 1000, 1200, 1400, 1600, 1800, or 2000 pg/ml or more. Little or no IL-4 or IL-2 corresponds to less than about 500 pg/ml, preferably less than about 250, 100, 75, or 50 pg/ml, or less.

The term "antigen" as used herein refers to a protein, or peptide, associated with a particular disease for which the cells of this invention are being used to modulate, or for use in any of the methods of this invention. In one embodiment, the term "antigen" may refer to a synthetically derived molecule, or a naturally derived molecule, which shares sequence homology with an antigen of interest, or structural homology with an antigen of interest, or a combination thereof. In one embodiment, the antigen may be a mimetope. A "fragment" of the antigen refers to any subset of the antigen, as a shorter peptide. A "variant" of the antigen refers to a molecule substantially similar to either the entire antigen or a fragment thereof. Variant antigens may be conveniently prepared by direct chemical synthesis of the variant peptide, using methods well-known in the art.

The term "subject" as used herein refers to a mammal, in particular a human being.

The term "effective amount" as used herein refers to an amount sufficient to cause a beneficial or desired clinical result (e.g. improvement in clinical condition).

The term "clone" or "clone population" as used herein refers to a population of differentiated cells being derived from a unique differentiated cell.

The term "treatment" or "treating" as used herein generally refers to a clinical intervention in an attempt to alter the natural course of the individual being treated, and may be performed during the course of clinical pathology. Desirable effects include, but are not limited to, alleviating symptoms, suppressing, diminishing or inhibiting any direct or indirect pathological consequences of the disease, lowering the rate of disease progression, ameliorating or palliating the disease state, and causing remission or improved prognosis.

The term "autoimmune disease" as used herein refers to an immune response directed against a self-antigen.

Patients having multiple sclerosis may be identified by criteria establishing a diagnosis of clinically definite multiple sclerosis. Briefly, an individual with clinically definite multiple sclerosis has had two attacks and clinical evidence of either two lesions or clinical evidence of one lesion and paraclinical evidence of another separate lesion. Definite multiple sclerosis may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose multiple sclerosis. The McDonald criteria include the use of MRI evidence of CNS impairment over time to be used in diagnosis of multiple sclerosis, in the absence of multiple clinical attacks. Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging). The EDSS is a means to grade clinical impairment due to multiple sclerosis. Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to multiple sclerosis). A decrease of one full step indicates an effective treatment.

Exacerbations are defined as the appearance of a new symptom that is attributable to multiple sclerosis and accompanied by an appropriate new neurologic abnormality. In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale. An annual exacerbation rate and proportion of exacerbation-free patients are determined.

Therapy can be deemed to be effective if there is a statistically significant difference in the rate or proportion of exacerbation-free or relapse-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, or 20 months is particularly noteworthy.

Clinical measurements include the relapse rate in one and two-year intervals, and a change in EDSS, including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images. MRI can be used to measure active lesions using gadolinium-DTPA-enhanced imaging or the location and extent of lesions using T2-weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of multiple sclerosis lesions can be determined by radiologists. Areas of lesions can be outlined and summed slice by slice for total lesion area. Three analyses may be done: evidence of new lesions, rate of appearance of active lesions, percentage change in lesion area. Improvement due to therapy can be established by a statistically significant improvement in an individual patient compared to baseline or in a treated group versus a placebo group.

Each case of multiple sclerosis displays one of several patterns of presentation and subsequent course. Most commonly, multiple sclerosis first manifests itself as a series of attacks followed by complete or partial remissions as symptoms mysteriously lessen, only to return later after a period of stability. This is called relapsing-remitting (RR) multiple sclerosis.

Primary-progressive (PP) multiple sclerosis is characterized by a gradual clinical decline with no distinct remissions, although there may be temporary plateaus or minor relief from symptoms.

Secondary-progressive (SP) multiple sclerosis begins with a relapsing-remitting course followed by a later primary-progressive course. Rarely, patients may have a progressive-relapsing (PR) course in which the disease takes a progressive path punctuated by acute attacks.

PP, SP, and PR are sometimes lumped together and called chronic progressive multiple sclerosis. A few patients experience malignant multiple sclerosis, defined as a swift and relentless decline resulting in significant disability or even death shortly after disease onset.

The Present Invention

The present invention relates to a composition comprising at least one Tr1 cell population directed against a multiple sclerosis-associated antigen.

In one embodiment of the invention, Tr1 cells may be obtained by
a) isolating a progenitor cell population from a subject,
b) obtaining a population of dendritic cells by culturing said progenitor cell population in the presence of IL-10
c) contacting cells of step b) with a CD4+ T lymphocyte population isolated from said subject in the presence of a multiple sclerosis-associated antigen to allow differentiation of CD4+ T cells directed to said antigen into the Tr1 cell population, and
d) recovering the Tr1 cell population from the step c).

In step b), IL-10 is present from 50 to 250 U/ml, preferably at 100 U/ml in the culture medium. Said method for obtaining Tr1 cells is described in Wakkach et al (Immunity 2003 May; 18(5):605-17).

Said method may also be carried out using Dexamethasone and Vitamin D3, or tolerogenised or immature DCs instead of the DCs of step b).

In another embodiment of the present invention, Tr1 cells may be obtained by:
a) culturing a CD4+ T cell population directed to a multiple sclerosis-associated antigen isolated from a subject in a media with an appropriate amount of IFN-α, and
b) recovering the Tr1 cell population.

IFN-α is preferably present in the media at 5 ng/ml. In the step a), the media may further comprise an appropriate amount of IL-10, preferably at 100 U/ml.

In step b), the Tr1 cell population is cultured in a media comprising IL-15 to allow proliferation, IL-15 being preferably at 5 ng/ml in the media. Said method for obtaining Tr1 cells is described in the U.S. Pat. No. 6,746,670.

In still another embodiment of the invention, Tr1 cells may be obtained by:
a) in vitro activating a CD4+ T cell population in presence of a multiple sclerosis-associated antigen, presented by artificial antigen presenting cells, and
b) recovering an activated CD4+ T cells comprising at least 10% of Tr1 cells.

Preferably, the artifical antigen presenting cells express a HLA II system molecule and a human LFA-3 molecule and don't express the co-stimulation molecules B7-1, B7-2, B7-H-1, CD40, CD23 and ICAM-1.

Said process, for obtaining Tr1 cells is described in the patent application WO02/092793.

In still another embodiment of the invention, Tr1 cells may be obtained by:
a) in vitro activating a CD4+ T cell population in presence of a multiple sclerosis-associated antigen and an appropriate amount of IL-10; and
b) recovering the Tr1 cell population.

Preferably, IL-10 is present in the media at 100 U/ml. Said method is described in Groux et al. (Nature 1997, 389 (6652):737-42).

In still another embodiment of the invention, antigen-specific Tr1 cells may be obtained by:
a) stimulating a leukocyte population or a peripheral blood mononuclear cell (PBMC) population with a multiple sclerosis-associated antigen,
b) recovering the antigen-specific Tr1 cell population from the stimulated population,
c) optionally expanding said antigen-specific Tr1 cell population.

Leukocytes encompass several types of cells, which are characterized by their importance, their distribution, their number, their lifetime and their potentiality. These types are the following: the polynuclear or granular leukocytes, among which one finds the eosinophilic, the neutrophilic and the basophilic leukocytes, and the mononuclear cells, or peripheral blood mononuclear cells (PBMCs), which are large white blood cells and consist in the cell types of the immune system (lymphocytes and monocytes). The leukocytes or the PBMCs can be separated from the peripheral blood by any method known to those skilled in the art. Advantageously, for the separation of the PBMCs, centrifugation may be used, preferably density gradient centrifugation, preferably discontinuous density gradient centrifugation. An alternative is the use of specific monoclonal antibodies. In certain embodiments PBMC are typically isolated from the whole blood product by means of Ficoll-Hypaque, using standard procedures. In other embodiments the PBMCs are recovered by means of leukapheresis. Said method is described in the patent application WO2007/010406.

In still another embodiment, Tr1 cells may be obtained by:
a) culturing a leukocyte population or a peripheral blood mononuclear cell (PBMC) population with mesenchymal stem cells in the presence of a multiple sclerosis-associated antigen,
b) recovering the Tr1 cell population.

Said method can also be carried out with naïve or memory T cells instead of PBMC or leukocytes.

The Tr1 cell population thus obtained may further be expanded by culture in presence of cytokines such as Interleukine-2 and Interleukine-4. Alternatively, Interleukine-15 and Interleukine-13 could also be used in Tr1 cell expansion cultures.

In the methods described above, Tr1 cells can be characterized by the identification method described in WO2005/000344. Said identification method of Tr1 cells is based on the detection of the simultaneous presence of expression products of genes coding CD4 molecule and molecules from the group comprising CD18 and/or CD11a, and CD49b. Tr1 cells can be identified and/or purified by Elisa, flow cytometry, or immunoaffinity methods with antibodies directed against said markers.

Tr1 cells can also be enriched by positive selection or negative selection using flow cytometry or magnetic beads. Such methods are also described in WO2005/000344.

In another embodiment of the present invention, the Tr1 cells directed to a multiple sclerosis-associated antigen may be expanded by the in vitro method described in WO2006/108882. Said method comprises:
a) cultivating at a temperature T1 inferior to 35° C., in a culture medium Mf, feeder cells such as insect feeder cells, said temperature T1 allowing the proliferation of feeder cells and said feeder cells expressing factors which interact with the following cell surface proteins:
the CD3/TCR complex,
the CD28 protein,
the IL-2 receptor,
the CD2 protein,
the IL-4 receptor,
b) contacting the feeder cells obtained in step a) cleared or not of their culture medium Mf, with the Tr1 cell population contained in the culture medium Mp, wherein said culture medium Mp does not initially contain the factors cited in step a), in order to obtain a mixture containing the Tr1 cell population, the feeder cells and the culture medium Mp, c) cultivating the mixture obtained at step b) at a temperature 12 which is at least 35° C., said temperature being chosen such that the Tr1 cell population proliferates and the feeder cells do not proliferate, d) recovering the Tr1 cell population such expanded.

Examples of factors which interact with the above mentioned cell surface proteins include
- a modified anti-CD3 antibody, wherein the anti-CD3 intracytoplasmic domain of the CD3 heavy chain is replaced with a transmembrane domain,
- the CD80 or CD86 protein,
- the IL-2 secreted by the feeder cells,
- the CD58 protein,
- an interleukin selected from the group comprising IL-4 and IL-13.

In a preferred embodiment of the present invention, said Tr1 cells directed to a multiple sclerosis associated antigen may be cloned by using conventional methods for cloning T cells.

In preferred embodiment of the present invention, said composition comprising at least one Tr1 cell population directed against a multiple sclerosis-associated antigen or at least one clone of Tr1 cell directed against a multiple sclerosis-associated antigen may be frozen to be stored.

In a preferred embodiment of the present invention, said multiple sclerosis-associated antigen is selected from the group comprising myelin basic protein (MBP), myelin associated glycoprotein (MAG), myelin oligodendrocyte protein (MOG), proteolipid protein (PLP), oligodendrocyte myelin oligoprotein (OMGP), myelin associated oligodendrocyte basic protein (MOBP), oligodendrocyte specific protein (OSP/Claudin11), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

Preferably, said multiple sclerosis-associated antigen is selected from the group comprising myelin basic protein (MBP), proteolipid protein (PLP) and myelin oligodendrocyte protein (MOG) peptides and fragments, variants and mixtures thereof.

More preferably, said multiple sclerosis-associated antigen is selected from the group comprising MBP 82-98, MBP 83-99, MBP 151-170 for HLA-DR2 positive subjects.

More preferably, said multiple sclerosis-associated antigen is selected from the group comprising MOG 35-55, MOG 21-40, MOG 41-60, MOG 71-90, MOG 81-100, MOG 111-130, MOG 63-37 for HLA-DR2 positive subjects.

More preferably, said multiple sclerosis-associated antigen is selected from the group comprising MBP 111-129, MBP 116-123 for HLA-DR4 positive subjects.

More preferably, said multiple sclerosis-associated antigen is selected from the group comprising MOG 21-40, MOG 97-108, MOG 71-90, MOG 181-200 for HLA-DR4 positive subjects.

Another object of the present invention is to provide a medicament comprising a composition as described here above.

The present invention also intends to provide a pharmaceutical composition comprising a composition as described here above in combination with one or more pharmaceutically acceptable carrier.

The pharmaceutically acceptable carriers useful herein are conventional. Remington's Pharmaceutical Sciences 16$^{th}$ edition, Osol, A. Ed. (1980) describes composition and formulations suitable for pharmaceutical delivery of the composition of the present invention. In general, the nature of the carrier will depend on the mode of administration being employed. For instance, parenteral formulations usually comprise injectable fluids that include pharmaceutically and physiologically acceptable fluids such as water, physiological saline, balanced salt solutions, aqueous dextrose, sesame oil, glycerol, ethanol, combinations thereof, or the like, as vehicle. The carrier and composition can be sterile, and the formulation suits the mode of administration. In addition to biological neutral carriers, pharmaceutical compositions to be administrated can contain minor amounts of non toxic auxiliary substances, such as wetting or emulsifying agents, preservatives, and pH buffering agents and the like, for example sodium acetate or sorbitan monolaurate. The composition can be a liquid solution, suspension, emulsion.

In one embodiment of the invention, said medicament or pharmaceutical composition as described here above consists essentially of at least one Tr1 cell population directed against a multiple sclerosis-associated antigen.

In another embodiment of the invention, said medicament or pharmaceutical composition as described here above consists essentially of at least one clone of a Tr1 cell population directed against a multiple sclerosis-associated antigen.

As used herein, "consists essentially of" refers to a medicament or a pharmaceutical composition, wherein at least 70%, preferably 75%, 80%, 85% or 90% of the cells present in the medicament or pharmaceutical composition are Tr1 cells directed against a multiple sclerosis-associated antigen, In another embodiment of the invention, said medicament or pharmaceutical composition as described here above consists of at least one Tr1 cell population directed against a multiple sclerosis-associated antigen or at least one clone of a Tr1 cell population directed against a multiple sclerosis-associated antigen.

The present invention relates to the use of a composition as described here above for the preparation of a medicament or a pharmaceutical composition for treating multiple sclerosis.

An object of the present invention is also a method for treating multiple sclerosis in a subject in need thereof, comprising administering to said subject an effective amount of a medicament as described here above or a pharmaceutical composition as described here above.

According to the invention, the pharmaceutical composition or medicament as described here above is for treating multiple sclerosis.

According to the invention, the pharmaceutical composition or medicament as described here above is for use in the treatment of multiple sclerosis.

According to the invention, said pharmaceutical composition or medicament is not used in combination with the soluble multiple sclerosis-associated antigen.

According to the invention, said pharmaceutical composition or medicament is not administrated to the subject together with or in combination with the soluble multiple sclerosis-associated antigen.

According to the invention, there is no need for a co-treatment with the soluble multiple sclerosis-associated antigen to which the Tr1 cells are directed.

The composition may be formulated for parenteral, intramuscular, intravenous, intra-peritoneal, injection, intranasal inhalation, lung inhalation, intradermal, intra-articular, intrathecal, or via the alimentary tract.

Preferably, the medicament or pharmaceutical composition of the invention may be administrated by intramuscular, intraperitoneal or intravenous injection, or by direct injection into the lymph nodes of the patient, preferably by intravenous injection.

The amount of Tr1 cells directed to a multiple sclerosis associated antigen effective in the treatment of multiple sclerosis will depend on the nature of the multiple sclerosis, and can be determined by standard clinical techniques. The precise dose to be employed in the formulation will also depend on the route of administration, and the seriousness of the disease or disorder, and should be decided according to the judgment of the practitioner and each individual's circumstances. Effective doses can be extrapolated from dose-response curves derived from in vitro or animal model test systems.

In one embodiment of the present invention, $10^4$/kg to $10^9$/kg cells are administered to the subject. Preferably $10^5$/kg to $10^7$/kg cells and more preferably about $10^6$/kg cells are administered to the subject.

In one embodiment of the invention, the subject is administrated with the medicament at the time when flare-up are demonstrated by a decline in the clinical status of the subject or at the time when inflammatory lesions can be visualized for example by MRI within the central nervous system.

In one embodiment of the invention, the subject is administrated once with the medicament or the pharmaceutical composition of the present invention.

In a second embodiment of the invention, the subject is administrated once a month with the medicament or the pharmaceutical composition of the present invention.

In a third embodiment of the invention, the subject is administrated once a quarter with the medicament or the pharmaceutical composition of the present invention.

In a fourth embodiment of the invention, the subject is administrated once to twice a year with the medicament or the pharmaceutical composition of the present invention.

In another embodiment of the present invention, the medicament or pharmaceutical composition to be administered to a subject in need thereof comprises Tr1 cells autologous to the cells of said subject.

This means that Tr1 cells will be administrated to the subject they come from or that precursors used for the production of Tr1 cells come from the subject the Tr1 cells will be administrated to.

In another embodiment of the present invention, the method for treating multiple sclerosis in a subject in need thereof comprises the administration to said subject of an effective amount of the medicament or the pharmaceutical composition of the invention in combination with one or more therapeutic agent used for treating multiple sclerosis.

The present invention relates to the use of the pharmaceutical composition or medicament of the invention, wherein the administration to said subject of an effective amount of the medicament or the pharmaceutical composition of the invention is in combination with one or more therapeutic agent used for treating multiple sclerosis.

Examples of therapeutic agents commonly used for treating multiple sclerosis are the following:
  interferons, e.g., human interferon beta-1a (e.g., AVONEX® or Rebif®) and interferon beta-Ib (BETASERON™); human interferon beta substituted at position 17; Berlex/Chiron);
  glatiramer acetate (also termed Copolymer 1, Cop-1; COPAXONE™; Teva Pharmaceutical Industries, Inc.); and derivatives,
  fumarates, e.g., dimethyl fumarate (e.g., Fumaderm®);
  Rituxan® (rituximab) or another anti-CD20 antibody, e.g., one that competes with or binds an overlapping epitope with rituximab;
  mitoxantrone (NOVANTRONE®, Lederle);
  a chemotherapeutic, e.g., clabribine (LEUSTATIN®), azathioprine (IMURAN®), cyclophosphamide (CYTOXAN®), cyclosporine-A, methotrexate, 4-aminopyridine, and tizanidine;
  a corticosteroid, e.g., methylprednisolone (MEDRONE®, Pfizer), prednisone;
  an immunoglobulin, e.g., Rituxan® (rituximab); CTLA4 Ig; alemtuzumab (MabCAMPATH®) or daclizumab (an antibody that binds CD25);
  statins;
  immunoglobulin G intravenous (IgGIV),
  Nataluzimab (Tysabri) anti-integrin alpha-4 antibody,
  the oral CC chemokine receptor 1 antagonist BX471 (ZK811752),
  FTY720 (fingolimod),
  antibodies or antagonists of human cytokines or growth factors, for example, TNF, LT, IL-1, IL-2, IL-6, IL-7, IL-8, IL-12, IL-15, IL-16, IL-17, IL-18, IL-23, EMAP-I1, GM-CSF, FGF, and PDGF.
  antibodies to cell surface molecules such as CD2, CD3, CD4, CD8, CD25, CD28, CD30, CD40, CD45, CD69, CD80, CD86, CD90 or their ligands.
  FK506, rapamycin, mycophenolate mofetil, leflunomide, non-steroidal anti-inflammatory drugs (NSAIDs), for example, phosphodiesterase inhibitors, adenosine agonists, antithrombotic agents, complement inhibitors, adrenergic agents, agents that interfere with signaling by proinflammatory cytokines as described herein, IL-I [beta] converting enzyme inhibitors (e.g., Vx740), anti-P7s, PSGL, TACE inhibitors, T-cell signaling inhibitors such as kinase inhibitors, metal loproteinase inhibitors, sulfasalazine, azathloprine, 6-mercaptopurines, angiotensin converting enzyme inhibitors,
  amantadine, baclofen, papaverine, meclizine, hydroxyzine, sulfamethoxazole, ciprofloxacin, docusate, pemoline, dantrolene, desmopressin, dexamethasone, tolterodine, phenyloin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline.
  Examples of combination therapies currently used are
  glatiramer acetate and albuterol,
  glatiramer acetate and minocycline,
  interferon-beta 1a and mycophenolate mofetil,
  BHT-3009 and atorvastatin, In a preferred embodiment of the present invention, the method for treating multiple sclerosis in a subject in need thereof comprises the administration to said subject of an effective amount of the medicament or the pharmaceutical composition of the invention in combination with one or more therapeutic agent in the group of interferon-beta, glatiramer acetate, mitoxantrone, cyclophosphamide, methotrexate, aziathropine or natalizumab.

The present invention relates to the use of the pharmaceutical composition or medicament of the invention, wherein the administration to said subject of an effective amount of the medicament or the pharmaceutical composition of the invention is in combination with one or more therapeutic agent in the group of interferon-beta, glatiramer acetate, mitoxantrone, cyclophosphamide, methotrexate, aziathropine or natalizumab.

In another embodiment, the present invention also relates to a method of treatment of multiple sclerosis in which a the medicament or the pharmaceutical composition of the invention is to be administrated to a subject in need thereof, wherein the subject does not respond adequately to, or is unlikely to respond adequately to, one or more therapeutic agent in the group of interferon-beta, glatiramer acetate, mitoxantrone, cyclophosphamide, methotrexate, aziathropine or natalizumab.

The present invention relates to the use of the pharmaceutical composition or medicament of the invention, wherein said subject does not respond adequately to, or is unlikely to respond adequately to, one or more therapeutic agent in the group of interferon-beta, glatiramer acetate, mitoxantrone, cyclophosphamide, methotrexate, aziathropine or natalizumab.

"Inadequate response", "does not respond adequately to", or "unlikely to respond adequately" refer to an actual or probable response by a subject which indicates that the therapy has been, or is likely to be, ineffective, toxic, or poorly tolerated insofar as the subject is concerned.

Subjects that do not respond adequately or are unlikely to respond adequately to conventional treatment for multiple sclerosis such as treatment with one or more therapeutic agent in the group of interferon-beta, glatiramer acetate, mitoxantrone, cyclophosphamide, methotrexate, aziathropine or natalizumab, can be identified by using the EDSS score (Expanded Disability Status Scale) as conventionally known by the person skilled in the art.

EXAMPLES

In the following description, all experiments for which no detailed protocol is given are performed according to standard protocol.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Experimental Procedures
Mice

C57Bl/6 mice were obtained from Janvier (Le Genest-St-Isle, France). MOG35-55 specific-TCR transgenic mice on a C57Bl/6 background were housed in the laboratory of Pr. Liblau (Inserm U563, Hôpital Purpan, Toulouse). All mice were 7- to 8-weeks old females.

Antibodies and Reagents

The following antibodies were used for mouse cell purification and characterization: anti-CD4 (H129-19) anti-CD62L (Mel-14), (BD-Pharmingen, Le Pont de Claix, France). $MOG_{35-55}$ peptide was from Bachem (Voisin-le-Bretonneux, France). IL-2 was obtained by Chiron Corporation (Emmeryville, Calif., USA). IL-4, IL-12 and anti-IL12 were purchased from R&D systems (Minneapolis, USA).

T-Cells Purification and Culture

The medium used for T cell cultures was Iscove medium (Invitrogen) supplemented with FCS, Yssel medium and β2-Mercaptoethanol (Sigma). Splenocytes from $MOG_{35-55}$-specific TCR transgenic mouse were first labeled with FITC-conjugated anti-CD62L and PE-conjugated anti-CD4. Then, $CD4^+CD62L^+$ T cells were sorted on a FACStar SE (Becton Dickinson, France). All populations were >98% pure on reanalysis. The mouse Th1, Th2 and Tr1 cell directed against $MOG_{35-55}$ were obtained after in vitro differentiation as followed: $2.5 \times 10^5$ Sorted $CD4^+CD62L^+$ T cells were cultured in the presence of $4.10^6$ irradiated syngeneïc splenocytes in 24-well plates and in presence of the $MOG_{35-55}$ peptide (10 μg/ml). IL-12 (20 ng/ml), IL-4 (40 ng/ml) plus anti-IL-12 (5 μg/ml) or IL-10 (50 ng/ml) was added for T cell differentiation into Th1, Th2 and Tr1 cells, respectively. Cells were cultured at 37° C., 5% CO2 and divided when required in medium supplemented with IL-2 (100 Ul/ml) for Th1 and IL-2 plus IL-4 (20 ng/ml) for Th2 and Tr1 cells. Alternatively, Tr1 cells were also divided in medium supplemented with IL-10 (5 ng/ml). T-cell populations were restimulated once a week during two or three weeks.

Cytokine Assays

Sandwich ELISAs were performed on 48 hours supernatants of anti-CD3 (10 μg/ml)+anti-CD28 (1 μg/ml) stimulated T-cell populations. Briefly, $5.10^5$ cells were activated with coated anti-CD3 and soluble anti-CD28 monoclonal antibodies in 96-well flat bottom plates and cultured 48 hours at 37° C., 5% $CO_2$. ELISAs were performed using anti-IL-4 (11B11), anti-IL-10 (2A5), anti-IFN-γ (XGM1.2), biotin anti-IL-4 (24G2), anti-IL-10 (SXC1), anti-IFN-γ (R4-6A2) (Pharmingen Becton Dickinson).

Experimental Autoimmune Encephalomyelitis

Experimental autoimmune encephalomyelitis was performed following the protocol described by Cua et al (J. Exp. Med, 1999). Briefly, C57BL/6 mice were injected intradermaly with 2.5 mg of Mouse spinal Cord Homogenates prepared in Complete Freund Adjuvent. After 2 days, mice were injected with 200 ng of Pertussis Toxin by intraperitoneal administration. The same regimen of immunization was repeated at J8 and J9 for Spinal Cord and Pertussis Toxin, respectively. Clinical scores were evaluated on a daily basis from Day 10 and are: 0=No disease; 1=Tail paralysis; 2=Hind limb weakness; 3=Hind limb paralysis; 4=Hind limb plus forelimb paralysis; 5=Moribund. T cell populations ($3.10^5$ cells/mouse) were injected once by intravenous route at day 9.

Results
Differentiation of ANTI-$MOG_{35-55}$ T Lymphocytes

We first differentiate anti-$MOG_{35-55}$ CD4+ T lymphocytes populations from naive CD4+ T lymphocytes isolated from anti-$MOG_{35-55}$ TCR transgenic mice. All lymphocytes from these mice bear a specific TCR that specifically recognize the peptide $MOG_{35-55}$ presented in the context of $H-2^b$ molecules. Naive cells ($CD4^+CD62L^+$) were sorted and activated in vitro with irradiated syngeneic splenocytes and the $MOG_{35-55}$ peptide. IL-12 was added to differentiate Th1 cells, IL-4 and anti-IL12 monoclonal antibodies were added to differentiate Th2 cells and IL-10 was added to differentiate Tr1 cells. After 2 or 3 weekly stimulations, cells were harvested and tested for their production of cytokines under anti-CD3+ anti-CD28 stimulation. Results are shown FIG. 1.

We observed that cells submitted to differentiation in the presence of IL-10 acquired the typical pattern of Tr1 cell cytokine production with high IL-10 and low IL-4 production. IL-4 stimulation of differentiating cells gave rise to Th2 cells showing equal production of IL-4 and IL-10 and no IFN-γ production. Despite a significant IL-10 production, IL-12 stimulation of differentiating cells gave rise to cells showing Th1 cytokine production profile with high production of IFN-γ and no IL-4 production.

In Vivo Suppressive Function of Anti-MOG$_{35-55}$ TR1 Cells

Figure 2:
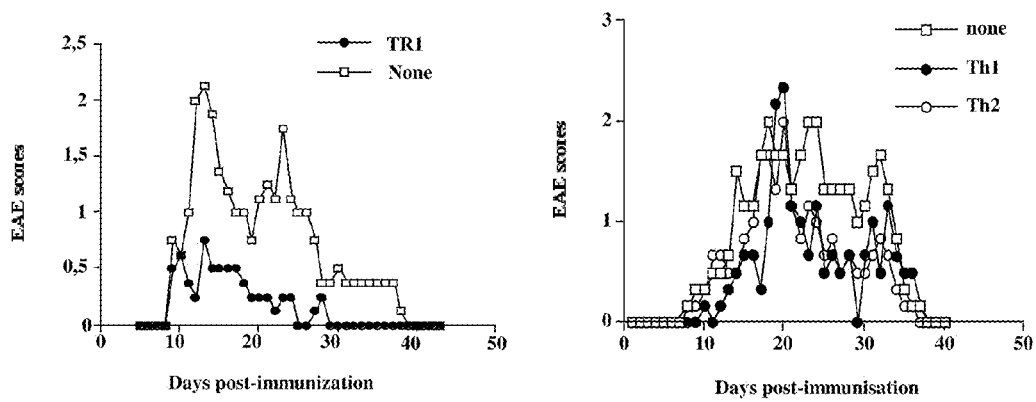
FIG. 2: Effect of anti-$MOG_{35-55}$CD4+T cells administration in EAE prone mice.

We next evaluated the effect of differentiated anti-MOO T cell populations on Experimental Autoimmune Encephalomyelitis in mice. For this purpose, C57Bl/6 mice were immunized with mouse spinal cord homogenates (msch) in complete freund adjuvant followed one day after by an intraperitoneal administration of Pertussis Toxin. The same regimen was repeated at day 8 and 9 for msch and pertussis toxin, respectively. Anti-MOG Th1, Th2 and Tr1 cell populations were injected intravenously to immunized mice at day 9 and the clinical score was evaluated once a day. FIG. 2 shows the impact of anti-MOG CD4 positive T cells on the evolution of experimental encephalomyelitis. We observed that Th1 and Th2 cells directed against the MOG$_{35-55}$ peptide had no significant effects on EAE induced by msch immunization. In contrast, administration of anti-MOG$_{35-55}$ Tr1 cells dramatically inhibits the development of EAE in immunized mice. Indeed, mice treated with Tr1 cells directed against myelin antigen developed a mild tail paralysis whereas control mice developed a loss of motor function of the hind limbs. Importantly, Tr1 administration not only inhibits the development of the illness but also prevent the relapse that occurs in non-T cell treated animals. A previous study (Barrat et al., J Exp Med, 2002) showed that anti-ovalbumin Tr1 cells are able to prevent EAE in mice. These suppressive effects were only achieved after intracranial instillation of ovalbumin showing that specific antigen activation of Tr1 cells in the brain is a prerequisite for their effector function. We thus wanted to evaluate whether a self-antigen, as a intrinsic component of the central nervous system could play such a role of suppressor cell activator. Our experiments answer positively to that question showing that Tr1 cells directed against a myelin antigen can inhibit encephalomyelitis in vivo. The MOG protein is one of the targets of pro-inflammatory cells in this mouse model of brain inflammation. The fact that Tr1 cells directed against the same antigen suppresses inflammation suggests that Tr1 treatment of inflammatory diseases could directly target the antigen for which tolerance was broken.

The invention claimed is:

1. A method for diminishing the loss of motor function and/or diminishing inflammation of the central nervous system in a human subject in need thereof, the method consisting of:
administering to said subject an effective amount of a pharmaceutical composition consisting of a Tr1 cell population directed against at least one human multiple sclerosis-associated antigen, in combination with one or more pharmaceutically acceptable carrier, or a medicament consisting of a Tr1 cell population directed against at least one human multiple sclerosis-associated antigen,
wherein said human multiple sclerosis-associated antigen is myelin basic protein, myelin associated glycoprotein, myelin oligodendrocyte protein, proteolipid protein, or a mixture thereof, and
the pharmaceutical composition or medicament comprises Tr1cells autologous to the cells of the subject.

2. The method according to claim 1, wherein $10^4$/kg to $10^9$/kg Tr1 cells are administered to the subject in need thereof.

3. The method according to claim 1, wherein said subject does not respond adequately to, or is unlikely to respond adequately to, one or more therapeutic agents selected from the group consisting of interferon-beta, glatiramer acetate, mitoxantrone, cyclophosphamide, methotrexate, aziathropine, and natalizumab.

4. The method according to claim 1, wherein said human multiple sclerosis-associated antigen is myelin oligodendrocyte protein.

5. The method according to claim 1, wherein the subject is HLA-DR2 positive, and wherein said human multiple sclerosis-associated antigen is selected from the group consisting of: MOG 35-55, MOG 21-40, MOG 41-60, MOG 71-90, MOG 81-100, MOG 111-130, and MOG 63-37 peptides.

6. The method according to claim 1, wherein the subject is HLA-DR4 positive, and wherein said human multiple sclerosis-associated antigen is selected from the group consisting of: MOG 21-40, MOG 97-108, and MOG 181-200 peptides.

7. A method for diminishing the loss of motor function and/or diminishing inflammation of the central nervous system in a human subject in need thereof, comprising:
administering to said subject an effective amount of a pharmaceutical composition consisting of a Tr1 cell population directed against at least one human multiple sclerosis-associated antigen in combination with one or more pharmaceutically acceptable carrier, or a medicament consisting of a Tr1 cell population directed against at least one human multiple sclerosis-associated antigen,
optionally in combination with one or more therapeutic agent used for treating multiple sclerosis,
wherein said human multiple sclerosis-associated antigen is myelin basic protein, myelin associated glycoprotein, myelin oligodendrocyte protein, proteolipid protein, or a mixture thereof,
said administration is without co-administration of the soluble antigen, and
the medicament or pharmaceutical composition comprises Tr1 cells autologous to the cells of said subject.

8. The method according to claim 7, wherein the administration to said subject of the effective amount of the medicament or the pharmaceutical composition is in combination with one or more therapeutic agent used for treating multiple sclerosis.

9. The method according to claim 8, wherein said one or more therapeutic agent is selected from the group consisting of interferon-beta, glatiramer acetate, mitoxantrone, cyclophosphamide, methotrexate, aziathropine, and natalizumab.

* * * * *